United States Patent [19]

Nelson

[11] Patent Number: 4,724,847
[45] Date of Patent: Feb. 16, 1988

[54] ANKLE BRACE

[76] Inventor: Ronald E. Nelson, 405 Sunset Ln., Cambridge, Minn. 55008

[21] Appl. No.: 64,405

[22] Filed: Jun. 22, 1987

[51] Int. Cl.⁴ .............................................. A61F 5/00
[52] U.S. Cl. .................................................. 128/80 H
[58] Field of Search ................. 128/80 H, 80 E, 80 F, 128/80 G, 80 A, 80 B, 80 D, 80, 166

[56] References Cited

U.S. PATENT DOCUMENTS

| 260,069 | 6/1882 | Wallace | 128/80 H |
|---|---|---|---|
| 325,280 | 9/1885 | Smadbeck et al. | |
| 332,727 | 12/1885 | McEwen | |
| 851,950 | 4/1907 | Le Mat | |
| 929,179 | 7/1909 | Wood | |
| 1,081,366 | 12/1913 | Collis | |
| 1,084,197 | 1/1914 | Collis | |
| 1,231,332 | 6/1917 | Collis | |
| 1,336,001 | 4/1920 | Trammer | 128/80 H |
| 2,994,322 | 8/1961 | Cullen et al. | 128/80 H |
| 3,298,365 | 1/1967 | Lewis | 128/80 R |
| 4,187,844 | 2/1980 | Caprio | 128/166 |
| 4,237,874 | 12/1980 | Nelson | 128/80 H |
| 4,527,556 | 7/1985 | Nelson | 128/80 H |
| 4,665,904 | 5/1987 | Lerman | 128/80 H |

FOREIGN PATENT DOCUMENTS 9531 7/1886 United Kingdom .

Primary Examiner—Edgar S. Burr
Assistant Examiner—Huong Q. Pham
Attorney, Agent, or Firm—Burd, Bartz & Gutenkauf

[57] ABSTRACT

An ankle brace to encompass the lower leg, ankle and upper foot of the user and adapted to substantially immobilize a badly injured ankle joint to protect it from aggravation during healing. The brace has a base with a plurality of lateral and medial generally upright pockets which carry rigid stay members contoured to anatomically conform to the ankle and foot structure. The brace has a tongue which also carries rigid stay members curved to conform to the adjacent foot portion. The stay members connected by the base together form a rigid structure in surrounding, immobilizing relationship to the ankle.

13 Claims, 8 Drawing Figures

U.S. Patent  Feb. 16, 1988  Sheet 1 of 2  4,724,847
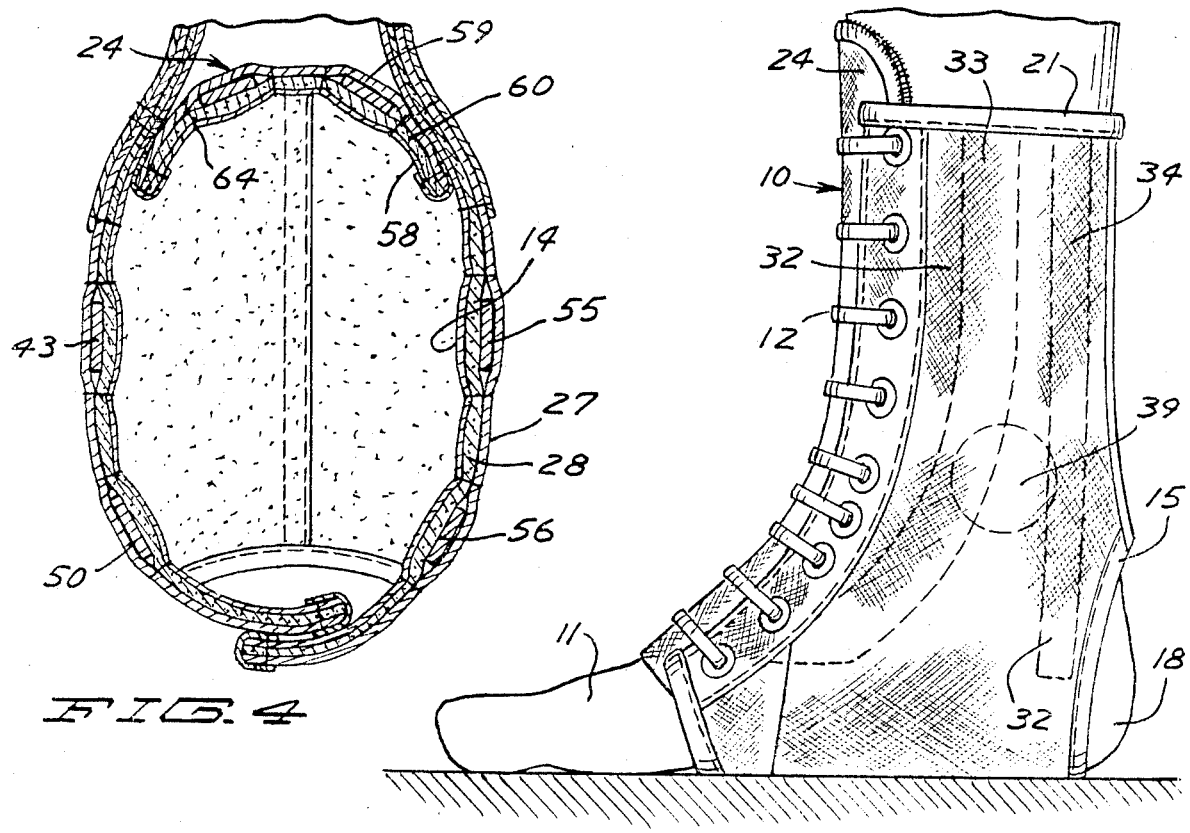
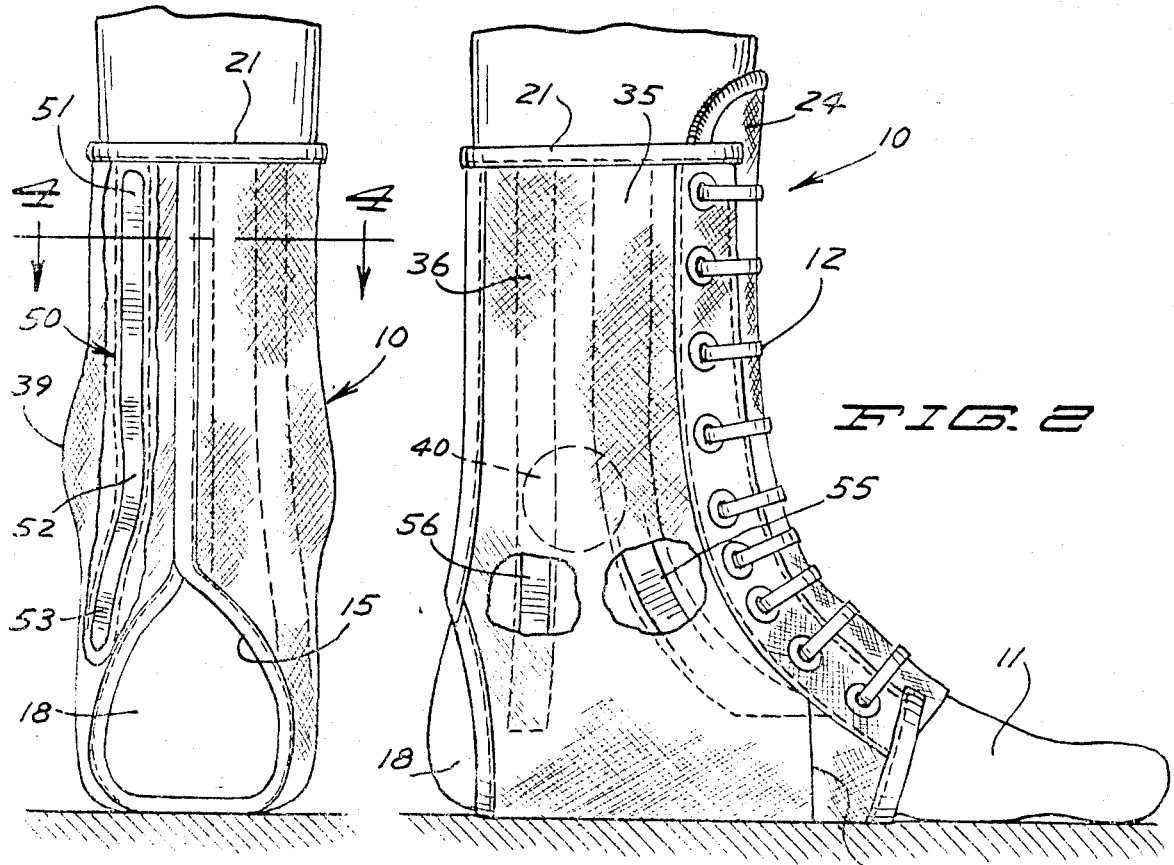

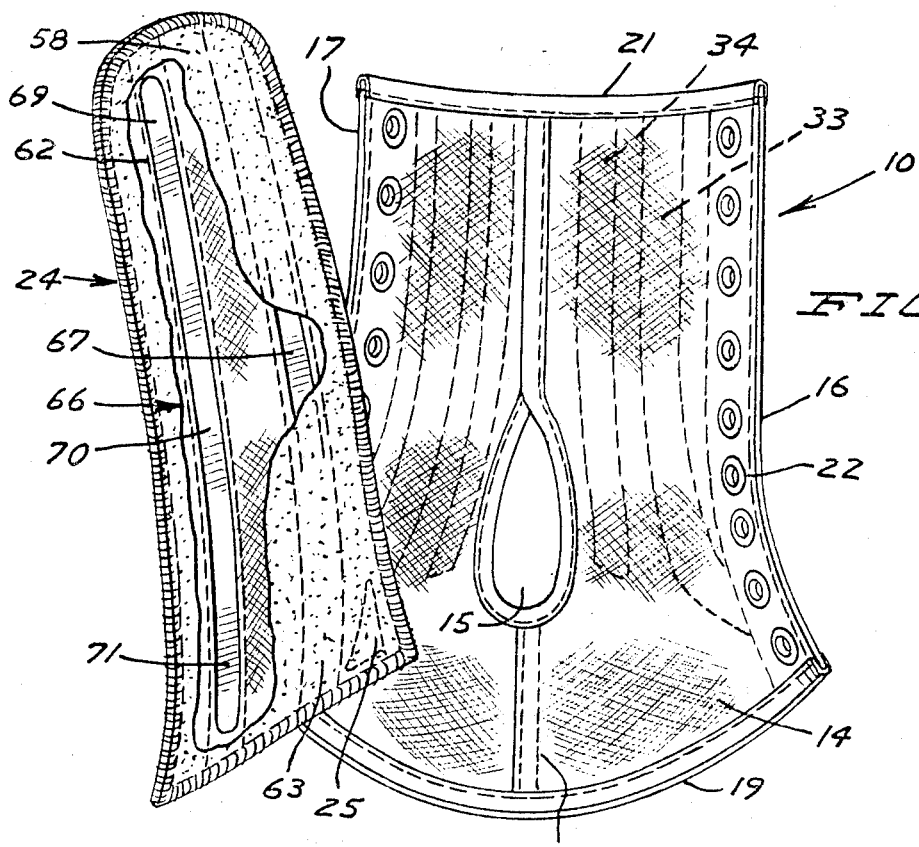
FIG.5
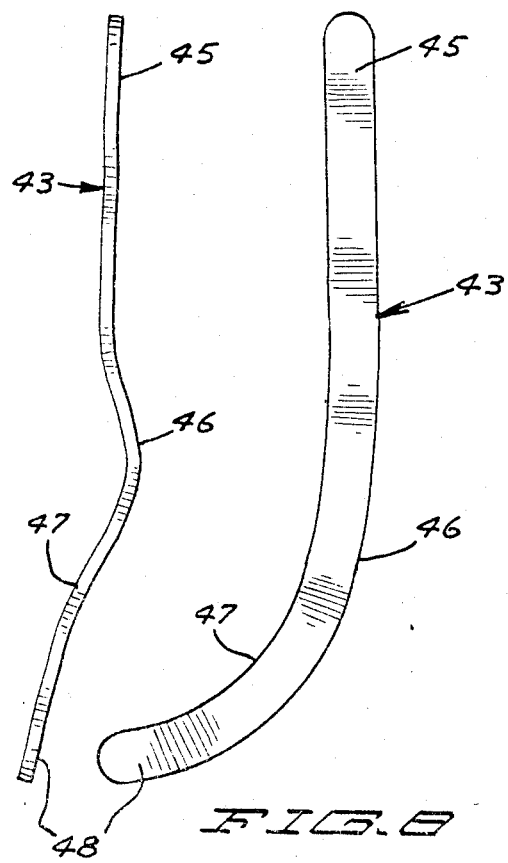
FIG.7
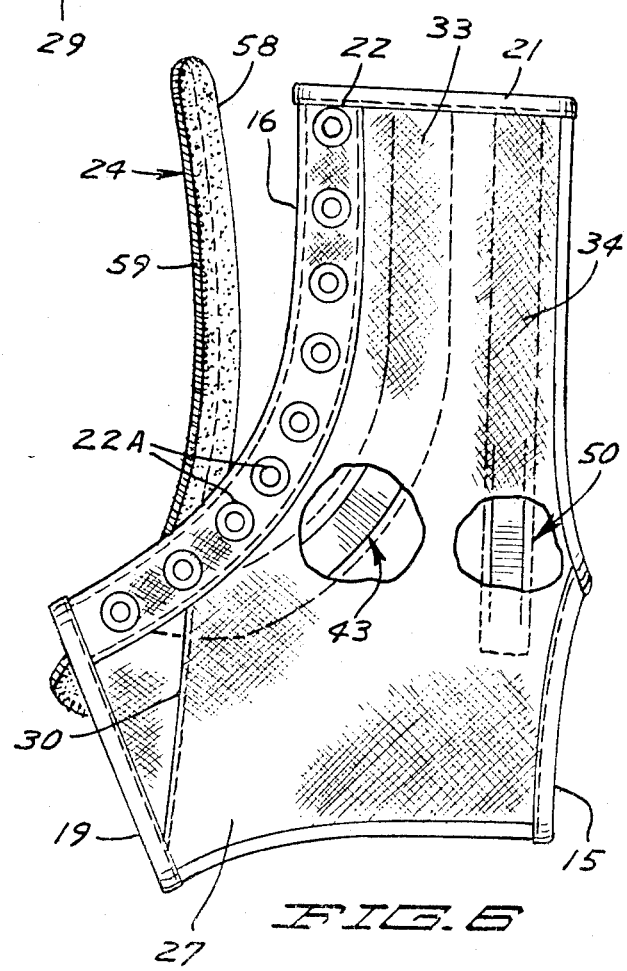
FIG.6
FIG.8

ANKLE BRACE

BACKGROUND OF THE INVENTION

The ankle is the most primitive joint in the body and is meant only for up and down movement, or movement in dorsiflexion and plantar flexion. It is not meant to rotate from side to side or to tilt inward and outward. As such, it is very stable and relatively resistent to serious injury. The two lower leg bones, the tibia and the fibula, join to form the top half of the ankle joint. The ankle is composed of seven bones known as the tarsal bones. One of these is the talus or ankle bone. The fibula and tibia are held tightly together by ligaments and form a mortice for reception of the talus. No muscle or tendons attach to the talus. When the ankle is injured and during healing, or in order to prevent further injury to the ankle and allow healing, it is desirable to restrain the ankle bone structure in proper relationship. To effect this end, various braces and wraps in the prior art have been provided. However, there is sometimes a need for more substantial immobilization of the ankle joint during the healing process.

SUMMARY OF THE INVENTION

The invention comprises an ankle brace conformable to the lower leg, ankle and upper foot of a wearer in order to substantially immobilize a badly injured ankle during healing. The brace includes a flexible base to be wrapped around the foot and laced up the front. The base conforms to the contours of the foot. A plurality of flexible pockets are located about the base in generally vertical orientation. Additional flexible pockets are located in the tongue. The flexible pockets in the base carry rigid stay members or ribs. The stays are purposely contoured in order to fit the various depressions and bulges that surround the foot. The tongue stays are also contoured in order to closely conform to that portion of the foot. Lateral and medial forward and rearward stays cooperate with the stays in the tongue to form a rigid structure around the ankle and closely conforming to it when installed thereon. The medial and lateral rear stays are generally flat and straight at the upper portion thereof, but at mid portion curve inwardly to conform to the depression immediately rearwardly of the lateral and medial malleolus.

IN THE DRAWINGS

FIG. 1 is a side elevational view of the medial side of a foot wearing an ankle brace according to the present invention;

FIG. 2 is a lateral side elevational view of the same foot and ankle brace of FIG. 1 with portions of the ankle brace removed for purposes of illustration;

FIG. 3 is a rear elevational view of the foot an ankle brace of FIGS. 1 and 2;

FIG. 4 is an enlarged sectional view of the ankle brace of FIG. 3 taken along the line 4—4 thereof;

FIG. 5 is a front plan view of the ankle brace of the invention in an open configuration to show the inside thereof;

FIG. 6 is a side elevational view of the ankle brace of the invention removed from the foot;

FIG. 7 is an end view of a forward stay used in the ankle brace of the invention; and FIG. 8 is a side elevational view of the forward stay of FIG. 7.

DESCRIPTION OF A PREFERRED EMBODIMENT

Referring to the drawings, there is shown in FIGS. 1 through 3 an ankle brace 10 worn on the right ankle and foot 11 of a wearer held securely thereon by lacing 12 in supportive relationship to the ankle joint. The ankle joint is the joint between the leg and the foot in which the tibia and the fibula above articulate with the talus below. The ankle is the region of the joint. The tarsus or ankle is composed of seven bones known as the tarsal bones. These bones, important in body support and locomotion, are known as the calcaneus, the talus, the nevicular, the cuboid, and the three cuneiform bones. The calcaneus is the largest of the tarsul bones. Its posterior extremity projects backward behind the ankle and forms the heel of the foot. The expanded portion of the posterior extremity is called the tuberosity of the calcaneus. The Achilles tendon extends upward from the tuberosity of the calcaneous. Just above the tuberosity of the calcaneous on the lateral and medial sides of the Achilles tendon are depressions. These depressions are located posterior to the lateral and medial malleolus and extend only a short distance upward along the ankle. The talus is the most superior of the tarsul bones and rests upon the upper surface of the calcaneous. The talus consists of a head, neck, and a body. Located on the superior surface of the body is a pulley-like articular surface called the trochlea. The upper part of the trochlea articulates with the end of the tibia, the medial part with the medial malleolus of the tibia, and the lateral part with the lateral malleolus of the fibula. The anterior end of the talus is called the head, and it articulates anteriorly with the navicular bone. The chief articulations between the talus and the calcaneous are behind the head. The neck separates the head and body of the bone. Located on the superior surface of the neck is a slight depression. The depression is manifest on lateral and medial sides of the foot just forward of the lateral and medial malleolus. These can be referred to as the lateral and medial talus neck depressions. Ankle brace 10 supports the ankle of the wearer with respect to these various ankle bones and lower legs so as to inhibit their relative movement substantially immobilize the ankle joint. Ankle brace 10 provides a cage-like structure around the ankle including rigid stays located circumferentially around the ankle which are curved to conform to the structure of the ankle region.

Referring to FIGS. 5 and 6, ankle brace 10 includes a first layer or base 14 of durable, flexible sheet-like material such as canvas having a soft side to be orientated toward the foot. Base 10 is configured to encompass the ankle joint and the ankle or adjacent lower leg portion, and the rear portion of the foot encompassing the arch and the instep. The posterior calcaneous or heel is accommodated in a hell opening 15. Closable forward edges 16, 17 of base 14 come together along the front superior foot surface. The forward edges 16, 17 are intermediately curved as shown in the transition region between the leg and foot to closely conform thereto. A bottom edge 19 extends from the lower ends of the forward edges 16, 17 and is slightly curved so as to encircle the foot 11 forming an opening for extension of the toes and front ball portion of the foot when the forward edges 16, 17 are brought together on the front superior foot surface. An upper edge 21 connects the upper ends of the forward edges 16, 17 and encircles the leg. The lower edge 15, upper edge 21 and heel opening 15 can have a reinforcement strip or hem as shown for purposes of durability.

Reinforcement strips are sewn to front edges 16, 17 and carry eyelets 22 for receipt of lacing 12. Lacing 12 is laced in and out of the eyelets 22 in the normal fashion and can be tied at the upper end thereof in the usual fashion in a bow knot. Eyelets are spaced apart along the forward edges 16, 17 and are closely spaced as the eyelets 22A in the vicinity of the ankle joint and the front superior foot surface. The closer spacing of the eyelets 22A in that vicinity provides a greater measure of support to the foot and lower leg portion. A tongue 24 is relatively rigid as will be described, and is connected at one corner 25 to the base 14 forming a hinge type connection so that it can be moved into and out of engagement with the front superior foot portion and ankle upon closure of the forward edges 16, 17 around the foot and ankle.

A second or outer layer 27 of a flexible, durable sheet-like material such as canvas is sewn to base 14 in substantially covering relationship to it. A foam layer 28 can be interposed between the outer layer 27 and base 14 in the vicinity of base 14 that wraps around the lower leg. Outer layer 27 is fixed to base 14 by stitching or seams 29 integral with the construction of base 14, as along the sole, along the back above heel opening 15, and along top edge 21 and forward edges 16, 17. Outer layer 27 has a forward edge 30 that is loose with respect to base 14.

A plurality of upright flexible pockets are formed betweem base 14 and outer layer 27 and carry rigid stay members purposely contoured to conform to the ankle region in order to form a composite structure to substantially immobilize the ankle when shoe 10 is securely installed thereon. As shown in FIG. 1, a first pocket 33 is formed as a forward medial pocket. A second pocket 34 is formed as a rearward medial pocket. As shown in FIG. 2, a third pocket is formed as a forward lateral pocket, and a fourth pocket is formed as a rearward lateral pocket. In the embodiments shown, the brace 10 is universal for installation on either a right or left foot whereby the lateral and medial pockets are symmetrical.

The first or forward medial pocket 33 extends from an upper forward medial region on the base 14 to a lower portion over the medial superior front surface. The upper part of the pocket is relatively straight. The pocket curves forwardly at the lower middle portion thereof. The lower middle portion of the pocket extends over the region occupied by the medial malleolus, indicated generally at 39 in FIG. 1. The lower end of the forward medial pocket 33 is forwardly and downwardly extended and terminates on an upper superior portion of the foot. The pocket extends over the medial foot depression just forward of the medial malleolus.

The third or forward lateral pocket extends on base 14 in symmetric relationship to the forward medial pocket 33 as shown in FIG. 2. The upper portion of the lateral forward pocket 35 is relatively straight. The pocket curves forwardly in the vicinity forward of the lateral malleolus and crosses the region of the foot having the lateral depression just forward of the lateral malleolus.

Rearward medial and lateral pockets 34 and 36 extend generally linearly from upper medial and lateral positions just beneath the upper edge 21 of brace 10 to lower ends positioned approximately midway along the heel opening 15. Medial rearward pocket 34 extends along a vertical axis passing just rearward of the vicinity of the medial malleolus 39 and over the medial talus neck depression. The rearward lateral pocket 36 passes rearward of the lateral malleolus 40 and over the lateral talus neck depression.

A first rigid stay or forward medial stay 43 is located in the forward medial pocket 33 (see FIG. 6) having a length and an intermediate forward curvature so as to fit well in the forward medial pocket 33. The forward medial stay 43 is shown in front and side elevation views in FIGS. 7 and 8. Stay 43 is substantially rigid, formed of a suitable metal or plastic with little flexibility. Stay 43 has a relatively flat and straight upper portion 45. Beginning at approximately the midpoint of its length, stay 43 has an outward bulge 46 as shown in FIG. 7 for accommodation of the forward portion of the medial malleolus. Beneath bulge 46, stay 43 has a slightly inwardly curved and forwardly curved region 47 to follow the foot depression forward of and beneath the medial malleolus and the curvature of the foot from the ankle. Stay 43 terminates at its lower extremity in a flat portion 48 which lies on the medial superior foot portion. Located in pocket 33 with brace 10 installed on a foot, the stay 43 closely follows the foot structure.

A second rigid stay or rear medial stay 50 is located in the rear medial pocket (FIGS. 3 and 6). Rear medial stay 50 is generally straight in side elevation. The top portion 51 of stay 50 is flat. Beginning approximately midway down the stay is an inward bulge 52 positioned to fit within the foot depression immediately behind and beneath the medial malleolus 39. An outwardly curved portion 53 extends from the inward bulge 52 and is configured to fit over the upper portion of the heel 18.

A third or forward lateral stay 55 is located in the forward lateral pocket 35, and a fourth or rear lateral stay 56 is located in the rear lateral pocket 36. The forward lateral and rearward lateral stays 55, 56 are configured symmetrical to the forward medial and rearward medial stays 33, 50.

Tongue 24 is comprised of an inner or base layer 58 and an outer layer 59, both comprised of flexible, durable material. A foam layer 60 can be interposed between the inner and outer layers 58, 59. The composite structure is held together by suitable sewing. A first or medial pocket 62 and a second generally parallel or lateral pocket 63 extend the length of tongue 24 and are formed by suitable stitching 64.

Tongue 24 has a generally concave intermediate profile in order to closely conform to the transition region between the lower leg, ankle and superior foot portion. Curved medial and lateral rigid tongue stays 66, 67 are located in the medial and lateral tongue pockets 62, 63. The medial and lateral tongue stays 66, 67 are alike in construction. As shown in FIG. 7, the medial tongue stay 66 has a relatively straight and flat upper portion 69. The central portion 70 is curved about a generally large radius, and the lower portion 71 is again relatively straight and flat. The stay 66 is formed of a rigid but mallable material such as metal. Upon normal wear, the stay 66 will not bend or deform. However, upon application of a suitable amount of force, stay 66 can be deformed or bent somewhat in order to be made to more readily conform to the superior foot portion upon which it is situated.

In use, the ankle brace 10 is installed upon the foot 11 by wrapping base 14 around the foot as shown in FIGS. 1 through 3. Base 14 and support layer 27 readily conform to the foot. Tongue 24 is placed over the front portion of the foot. The edges of tongue 24 are covered by the forward edges 16, 17 of base 14. Base 14 and outer layer 27, with the tongue 24 in place and lacing 12 tightened, provide good support to the ankle. With the medial and rearward stays 43, 50, and the lateral forward and rearward stays 55, 56 in place, together with the medial and lateral tongue stays 66, 67, a relatively rigid structure is formed in conforming relationship about the ankle region. The base and tongue hold the rigid stays in place with respect to the foot and ankle. The rigid stays hold the foot and ankle structure immobile. The stays conform to the adjacent contours of the foot and ankle structure which adapts them more readily to be rigidly secured with respect to the structure and prevent relative movement of the various bones with respect to one another.

While there has been shown and described a preferred embodiment of ankle brace of the present invention, it will be apparent that certain deviations and modifications can be had without departing from the scope and spirit of the invention.

The embodiments of the invention in which an exclusive property or privilege is claimed are defined as follows:

1. An ankle brace to be worn on a foot and ankle in covering relationship to the forward lateral and medial and rearward lateral and medial depressions of the foot to substantially immobilize the ankle, said brace comprising:
    a base of flexible sheet-like material shaped to encompass the ankle region from approximately the lower leg to at least the middle portion of the foot;
    said base having a plurality of generally upright pockets, including a forward medial pocket having an upper end at a forward medial location on the base, extending downward to an intermediate forwardly curved portion, and to a lower end at the medial superior foot surface and passing over the forward medial foot depression, and a rearward medial pocket with an upper end at a rearward medial location on the base and extending downward to a lower end proximate the heel of the foot and passing over the rearward medial depression of the foot when the base is installed on a foot and ankle;
    a forward lateral pocket having an upper end at a forward lateral location on the base extending downward to an intermediate forwardly curved portion, and to a lower end at the lateral superior foot surface and passing over the forward lateral foot depression, and a rearward lateral pocket with an upper end at a rearward lateral location on the base and extending downward to a lower end proximate the heel of the foot and passing over the rearward lateral depression of the foot when the base is installed on a foot and ankle;
    a plurality of rigid stays located in said pockets including a forward medial stay located in the forward medial pocket and a forward lateral stay located in the forward lateral pocket, a rear medial stay located in the rearward medial pocket, and a rearward lateral stay located in the rear lateral pocket;
    each forward stay configured with a straight flat upper portion in the upper portion of the pocket, an outward bulge located at an intermediate portion for accommodation of a forward malleolus portion of the foot, and an inwardly and forwardly curved lower region to follow the forward foot depression and conform to the shape of the pocket;
    each rear stay configured with a flat upper upper portion, an intermediate inward bulge to follow the rear foot depression, and an outward curved portion extended from the inward bulge configured to fit over the upper portion of the heel.

2. The ankle brace of claim 1 wherein: said base has closable forward edges that come forward each other about the front of the foot, and including a tongue pivotally connected to the base proximate one of the edges and movable to a position in covering relationship to the front of the foot, said tongue having elongate lateral and medial tongue pockets, and elongate lateral and medial tongue stays located in the tongue pockets, said tongue stays having an intermediate concave curvature to conform to the curvature transition between the ankle and foot.

3. The ankle brace of claim 2 including: an outer layer of sheet-like material fixed to the base, and means forming said pockets between the base and the outer layer.

4. The ankle brace of claim 3 including: a foam layer interposed between the base and the outer layer.

5. The ankle brace of claim 1 wherein: said base has first and second forward edges that wrap around the ankle and foot, and an upper edge that wraps around the lower leg portion, a bottom edge that wraps around an intermediate foot portion, and a heel opening at the rear thereof for accommodation of the heel, said forward edges coming together over the front of the foot, ankle and lower leg, means for securing the forward edges with respect to one another, a tongue having a concave profile hingedly fixed to the base and closable over the front of the ankle and foot between the front edges, said tongue having medial and lateral tongue pockets which extend from the upper ankle region to the superior foot portion on medial and lateral sides when the tongue is in covering relationship to the front of the foot, and medial and lateral tongue stays located in the medial and lateral tongue pockets, said tongue stays having said concave profile.

6. The ankle brace of claim 5 including: an outer layer of sheet-like material fixed to the base, and means forming said pockets on the base between the base and the outer layer.

7. The ankle brace of claim 6 wherein: said pockets are sewn between the base and the outer layer.

8. The ankle brace of claim 6 wherein: said means for securing the forward edges with respect to one another comprises a plurality of eyelets on the first forward edge, a corresponding plurality of eyelets on the second forward edge, and a lace trained through the eyelets.

9. An ankle brace to be worn on a foot and ankle to substantially immobilize the ankle, comprising:
    a base of flexible sheet-like material configured to encompass the ankle region from approximately the lower leg to at least the mid portion of the foot, said base having first and second forward edges that wrap around the ankle and the foot and come together along the front of the foot, an upper edge that wraps around the lower leg portion, and bottom edge that wraps around the intermediate foot portion, with a heel opening at the rear thereof for accommodation of the heel, means for securing the first and second forward edges together;
    a tongue pivotally connected to the base proximate one of the forward edges and movable to a position in covering relationship to the front of the foot when the base is installed on the foot;

said base having a plurality of generally upright pockets comprised as a front and rear medial pockets and front and rear lateral pockets, said front pockets extending from a location proximate the upper edge of the base, having an intermediate forward curvature and extending to a forward superior location on the foot;

said rear pockets extending from a rearward lateral and medial location of a base near the upper edge downwardly to a location over the heel when the base is installed on the foot;

each of said pockets having a rigid stay, each rigid stay having a relatively straight upper portion located in the upper portion of the pocket and an inwardly curved lower portion conforming to a foot depression;

said tongue having lateral and medial elongate pockets, lateral and medial elongate tongue stays located in said pockets, said tongue stays being comprised as rigid members having intermediate convex curvature to conform to the transition area between the foot and the lower leg over the ankle.

10. The ankle brace of claim 9 wherein: said forward stays and the forward lateral medial pockets are forwardly curved over the superior portion to conform to the transition region between the leg and the foot, and said rear stay members are outwardly curved beneath the inward curve to conform to the portion of the heel below the rearward lateral and medial foot depressions.

11. The ankle brace of claim 10 including: an outer layer of sheet-like material fixed to the base, said pockets on the base being formed between the base and the sheet-like material.

12. The ankle brace of claim 11 including: a foam layer interposed between the base and the outer layer.

13. The ankle brace of claim 11 wherein: said means to secure the first and second forward edges of the base together comprises a plurality of eyelets located along the first and second forward edges, and a lace drawn through the eyelets adapted to be drawn tightly and secured on the front of the foot.

* * * * *